(12) United States Patent
Alnamasi

(10) Patent No.: US 10,760,935 B1
(45) Date of Patent: Sep. 1, 2020

(54) FLUID EVALUATION DEVICES FOR OIL AND GAS APPLICATIONS

(71) Applicant: Saudi Arabian Oil Company, Dhahran (SA)

(72) Inventor: Fahad Sadon A. Alnamasi, Rahima (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/277,518

(22) Filed: Feb. 15, 2019

(51) Int. Cl.
| G01F 23/00 | (2006.01) |
| B65D 90/48 | (2006.01) |
| G01F 23/02 | (2006.01) |
| B01D 17/02 | (2006.01) |

(52) U.S. Cl.
CPC ..... *G01F 23/0046* (2013.01); *B01D 17/0208* (2013.01); *B65D 90/48* (2013.01); *G01F 23/0007* (2013.01); *G01F 23/02* (2013.01)

(58) Field of Classification Search
CPC .. G01F 23/02; G01F 23/0046; G01F 23/0007; B01D 17/0208
See application file for complete search history.

(56) References Cited

U.S. PATENT DOCUMENTS

| 3,250,122 A | 5/1966 | Doering |
| 5,070,725 A | 12/1991 | Cox et al. |
| 5,154,312 A * | 10/1992 | Robbins ............... B65D 90/105 220/724 |
| 7,523,647 B2 | 4/2009 | Scott |
| 7,775,085 B2 | 8/2010 | Scott |
| 9,664,548 B2 | 5/2017 | Henry et al. |

FOREIGN PATENT DOCUMENTS

| CN | 202376806 | 8/2012 | |
| CN | 202376806 U * | 8/2012 | ............. B01D 17/02 |
| RU | 2183317 | 6/2002 | |
| WO | 8300553 | 2/1983 | |
| WO | 2007113668 | 10/2007 | |

OTHER PUBLICATIONS

Joneng Valves Co. product webpage for "Stainless steel ball type sight glass" 2012 (Year: 2012).*
International Search Report and Written Opinion issued in International Application No. PCT/US2019/021338 dated Dec. 2, 2019, 15 pages.

* cited by examiner

*Primary Examiner* — Paul M. West
(74) *Attorney, Agent, or Firm* — Fish & Richardson P.C.

(57) ABSTRACT

A fluid evaluation device for analyzing a fluid content within a container includes first and second fluid sampling conduits passing laterally into the container and respectively extending to first and second depths within fluid stored in the container, a common fluid conduit to which the first and second fluid sampling conduits extend for receiving fluid flowing out of the container through either of the first or second sampling conduits, and an optical device positioned along the common fluid conduit and including a viewing window for observing fluid flowing therethrough from the common fluid conduit.

31 Claims, 5 Drawing Sheets

FLUID EVALUATION DEVICES FOR OIL AND GAS APPLICATIONS

TECHNICAL FIELD

This disclosure relates to fluid evaluation devices for determining a water cut of a crude oil tank.

BACKGROUND

At hydrocarbon facilities, crude oil is produced from oil wells and is subsequently transported to a gas-oil separation plant (GOSP) for treatment. Once gas is separated from the crude oil at the GOSP, the crude oil is pumped from the GOSP to tanks for storage and export. Typically, water is mixed with crude oil flowing through pipes as the crude oil leaves a GOSP. Once the crude oil is stored in a tank, the mixture of crude oil and water will separate after a certain settling time. The specific weight and the density of crude oil is less than that of water. Therefore, the water will settle to a bottom region of the tank, and the crude oil will settle on top of the water. A level of the interface between the water and the crude oil will depend on amounts of crude oil and water within the tank. For crude oil within a tank to be sold, a water cut of the tank (for example, the volume of water present in the tank) must be below an acceptable threshold volume. Thus, the volume of water above the threshold volume is drained, and the crude oil remaining in the tank is subsequently shipped. The threshold volume typically corresponds to a certain height of a water level above a floor of the tank.

In order for excess water to be drained from the tank, the water cut in the tank must first be determined. Conventionally, a dip gauge is used to determine a water cut of a tank. In use, an operator climbs to a roof of the tank and drops a dip gauge into the tank while holding on to an end of a deployment cable to which the dip gauge is attached. The dip gauge includes a base material that changes color upon chemically reacting with water. Accordingly, once the dip gauge reaches the bottom of the tank, a height of the dip gauge at which the base material changes color reflects a water level in the tank. The operator pulls the dip gauge from the tank and measures a length of a reacted portion of the dip gauge, where each increment of length of the reacted portion corresponds to a certain volume of water in the tank. Deploying a dip gauge to measure the water cut is associated with several operational, health, and safety risks.

SUMMARY

This disclosure relates to fluid evaluation devices for determining a water cut of a crude oil tank. Such a fluid evaluation device is designed to be installed to a manhole of the crude oil tank that is located near a ground level of the crude oil tank. The fluid evaluation device includes an access cover that is attachable to the manhole, multiple pipes that extend through the access cover for sampling fluid within the crude oil tank, and multiple level valves respectively located on exterior portions of the pipes for selectively closing the pipes. The pipes respectively include L-shaped interior portions of differing vertical lengths that extend from the cover into the crude oil tank to respective depths within the crude oil tank. The fluid evaluation device further includes a common header pipe to which the exterior portions of the pipes extend, an optical device positioned along the common header pipe for visualizing fluid flowing from any of the pipes, and a drain pipe that extends from the optical device to a drain line of the crude oil tank.

The optical device is formed as a "t" structure and includes two opposing glass viewing windows through which fluid flowing from the pipes can be easily observed at a location near the ground level for determining a water cut of the fluid within the crude oil tank. The fluid evaluation device can be mechanically installed to the manhole in a quick, simple manner. Furthermore, using the fluid evaluation device eliminates a need for an operator to climb to a roof of the crude oil tank to perform conventional water cut measurement techniques and accordingly eliminates associated risks of extensive physical exertion, falling, and exposure to toxic gases, among other risks and drawbacks.

In one aspect, a fluid evaluation device for analyzing a fluid content within a container includes first and second fluid sampling conduits passing laterally into the container and respectively extending to first and second depths within fluid stored in the container, a common fluid conduit to which the first and second fluid sampling conduits extend for receiving fluid flowing out of the container through either of the first or second sampling conduits, and an optical device positioned along the common fluid conduit and including a viewing window for observing fluid flowing therethrough from the common fluid conduit.

Embodiments may provide one or more of the following features.

In some embodiments, the first and second fluid sampling conduits have an L-shape.

In some embodiments, the fluid evaluation device further includes a plate through which the first and second fluid sampling conduits pass laterally into the container.

In some embodiments, the plate is configured to cover an access opening of the container.

In some embodiments, the fluid evaluation device further includes first and second valves respectively arranged along the first and second fluid sampling conduits for selectively opening and closing the first and second fluid sampling conduits to fluid flow.

In some embodiments, the fluid evaluation device further includes first and second markings respectively indicating or corresponding to the first and second depths of the first and second fluid sampling conduits.

In some embodiments, the first and second fluid sampling conduits have vertical lengths in a range of about 50 cm to about 200 cm.

In some embodiments, a difference in a vertical length between the first and second fluid sampling conduits is about 2 cm to about 10 cm.

In some embodiments, the first and second depths are located in a range of about 2.5 cm to about 150 cm above a floor of the container.

In some embodiments, the first and second fluid sampling conduits are spaced laterally from each other by about 4 cm to about 8 cm.

In some embodiments, the fluid evaluation device further includes a discharge fluid conduit coupled to the common fluid conduit for receiving the fluid flowing from the common fluid conduit and directing the fluid away from the container.

In some embodiments, the optical device is arranged between the common fluid conduit and the discharge fluid conduit such that the optical device is located downstream of the common fluid conduit and upstream of the discharge fluid conduit.

In some embodiments, the viewing window is a first viewing window, and the optical device further includes a second viewing window disposed opposite the first viewing window.

In some embodiments, the optical device further includes a body having a t-shape, and the first and second viewing windows are disposed at opposite ends of the body.

In some embodiments, the viewing window includes a glass viewing window.

In some embodiments, the optical device is positioned at a height of about 100 cm to about 200 cm above a ground level at which the container is positioned.

In some embodiments, the fluid evaluation device further includes one or more additional fluid sampling conduits passing laterally into the container, respectively extending to one or more depths within the fluid stored in the container, and extending to the common fluid conduit.

In some embodiments, the container contains crude oil and water.

In some embodiments, the fluid content of the container is a water cut of a crude oil tank.

In another aspect, a method of analyzing a fluid content within a container includes flowing a first fluid at a first depth within the container out of the container through a first fluid sampling conduit of a fluid evaluation device and into a common fluid conduit of the fluid evaluation device, flowing the first fluid out of the common fluid conduit and through an optical device of the fluid evaluation device, observing the first fluid through a viewing window of the optical device and determining that the first fluid is a first color, flowing a second fluid at a second depth within the container out of the container through a second fluid sampling conduit of the fluid evaluation device, into the common fluid conduit, and through the optical device, observing the second fluid through the viewing window and determining that the second fluid is a second color, and determining an amount of the first fluid or the second fluid in the container based on the second depth.

Embodiments may provide one or more of the following features.

In some embodiments, the optical device is located at about 100 cm to about 200 cm above a ground level at which the container is positioned.

In some embodiments, the method further includes stopping a flow of the first fluid out of the container after determining that the first fluid is the first color and before flowing the second fluid out of the container.

In some embodiments, the method further includes reading an indication of the second depth from a marking on the fluid evaluation device.

In some embodiments, the first color is black, the first fluid is crude oil, and the second fluid is water.

In some embodiments, the second depth is lower than the first depth.

In some embodiments, the second color is black, the first fluid is water, and the second fluid is crude oil.

In some embodiments, the first depth is lower than the second depth.

In some embodiments, the viewing window is a first viewing window, and the optical device further includes a second viewing window disposed opposite the first viewing window.

In some embodiments, the optical device further includes a body having a t-shape, and the first and second viewing windows are disposed at opposite ends of the body.

In some embodiments, determining an amount of the first fluid or the second fluid in the container includes determining a water cut of a crude oil tank.

The details of one or more embodiments are set forth in the accompanying drawings and description. Other features, aspects, and advantages of the embodiments will become apparent from the description, drawings, and claims.

DETAILED DESCRIPTION

Figure 1:
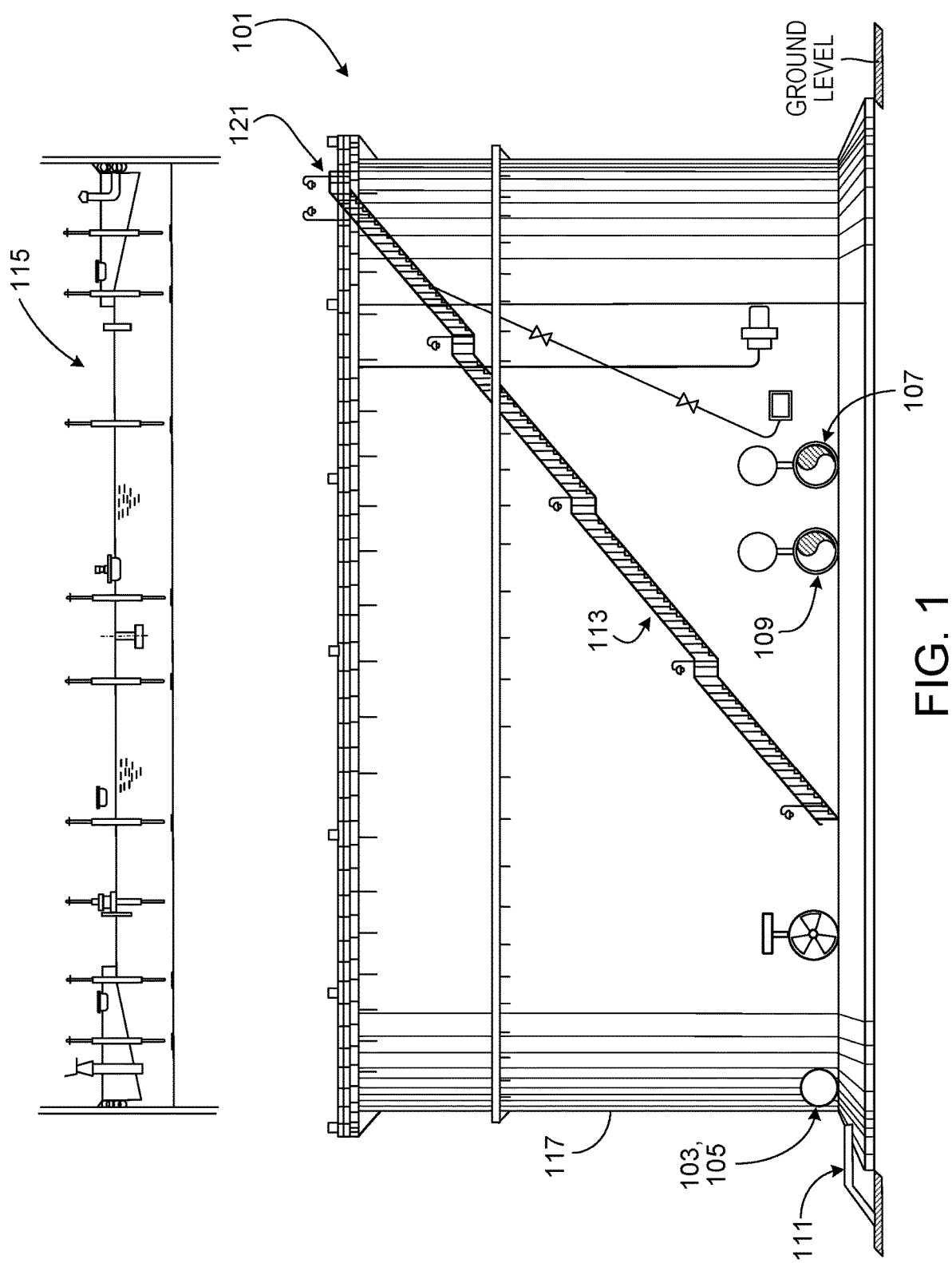
FIG. 1 is a side view of an example tank that contains crude oil and water.

FIG. 1 illustrates a tank 101 that contains crude oil and a certain amount of water associated with the crude oil. The tank 101 includes multiple manholes 103 (for example, access openings) and respective access covers 105 located near or at a ground level of the tank 101, an inlet access 107 for loading the tank 101, an outlet access 109 for unloading the tank 101 via suction after the water content within the tank 101 has been drained, a drain line 111 for passing an oil and water mixture to a drainage system (e.g., a slop system), a stairway 113, and a floating roof 115 (exploded from a wall 117 of the tank 101 in FIG. 1), among other components. The stairway 113 provides access to a top platform 121 of the tank 101 at which an operator can manually drop a dip gauge into the tank 101 to determine a water cut of the tank 101. The top platform 121 may be approximately level with the floating roof 115, or the top platform 121 may be spaced apart from (for example, positioned above) the floating roof 115, depending on a fluid level within the tank 101. The tank 101 typically has a height (for example, defining a height of the top platform 121) of about 15 meters (m) to about 30 m, an internal diameter of about 10 m to about 70 m, and a capacity (for example, an interior holding volume) of about 5,000,000 liters (L) to about 250,000,000 L.

Figure 2:
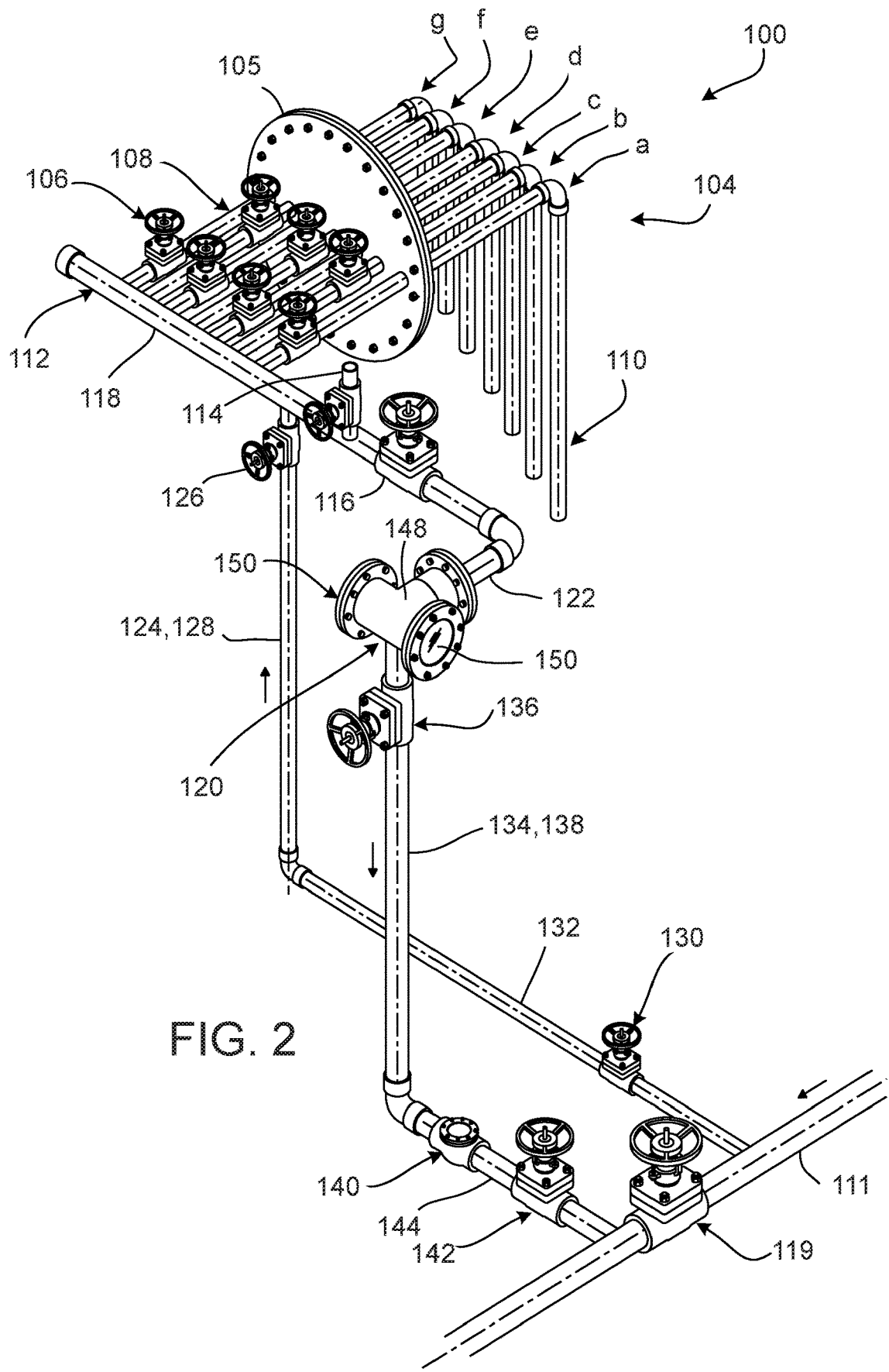
FIG. 2 is a perspective view of a fluid evaluation device that can be installed to the tank of FIG. 1.
Figure 3:
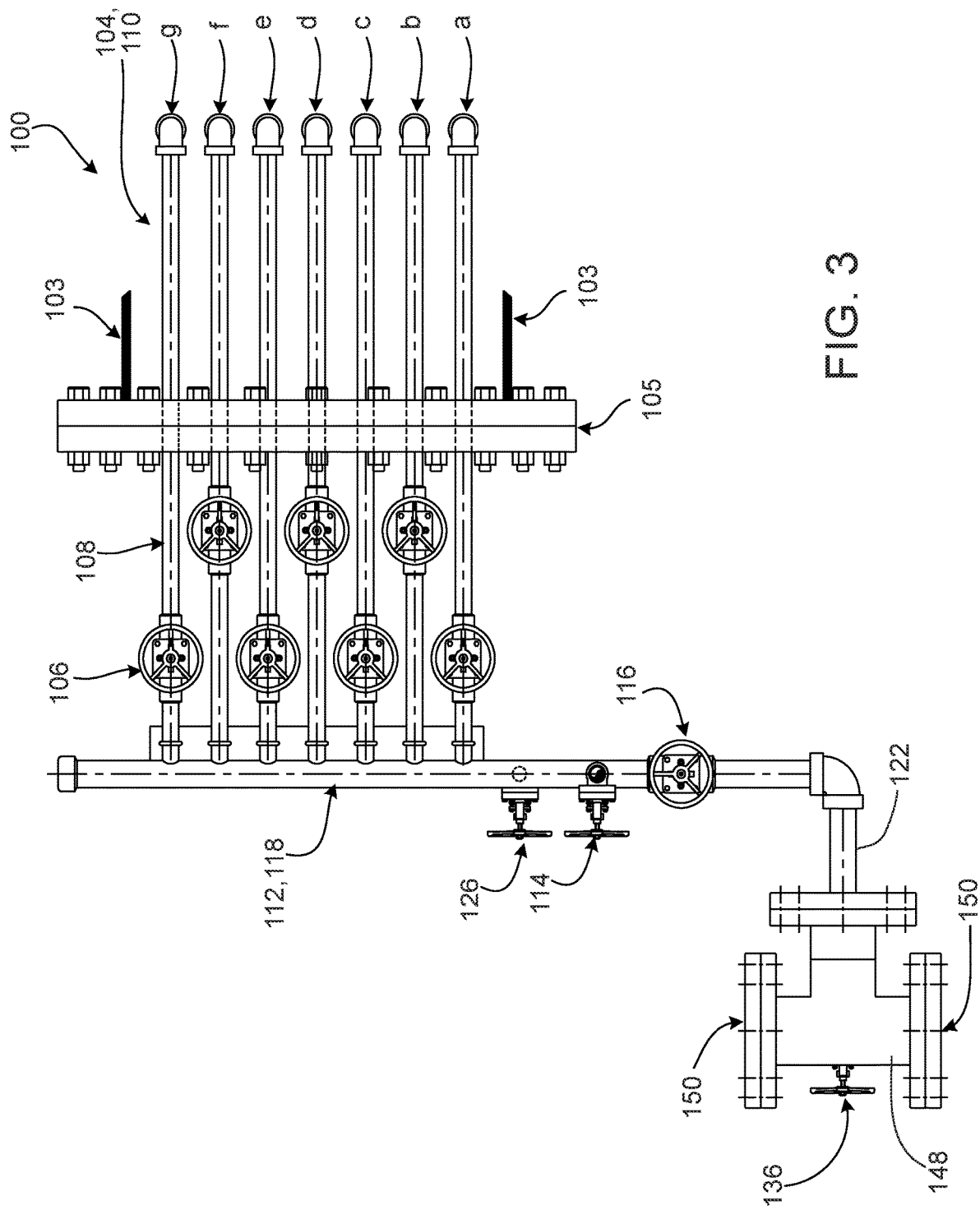
FIG. 3 is a top view of the fluid evaluation device of FIG. 2.
Figure 4:
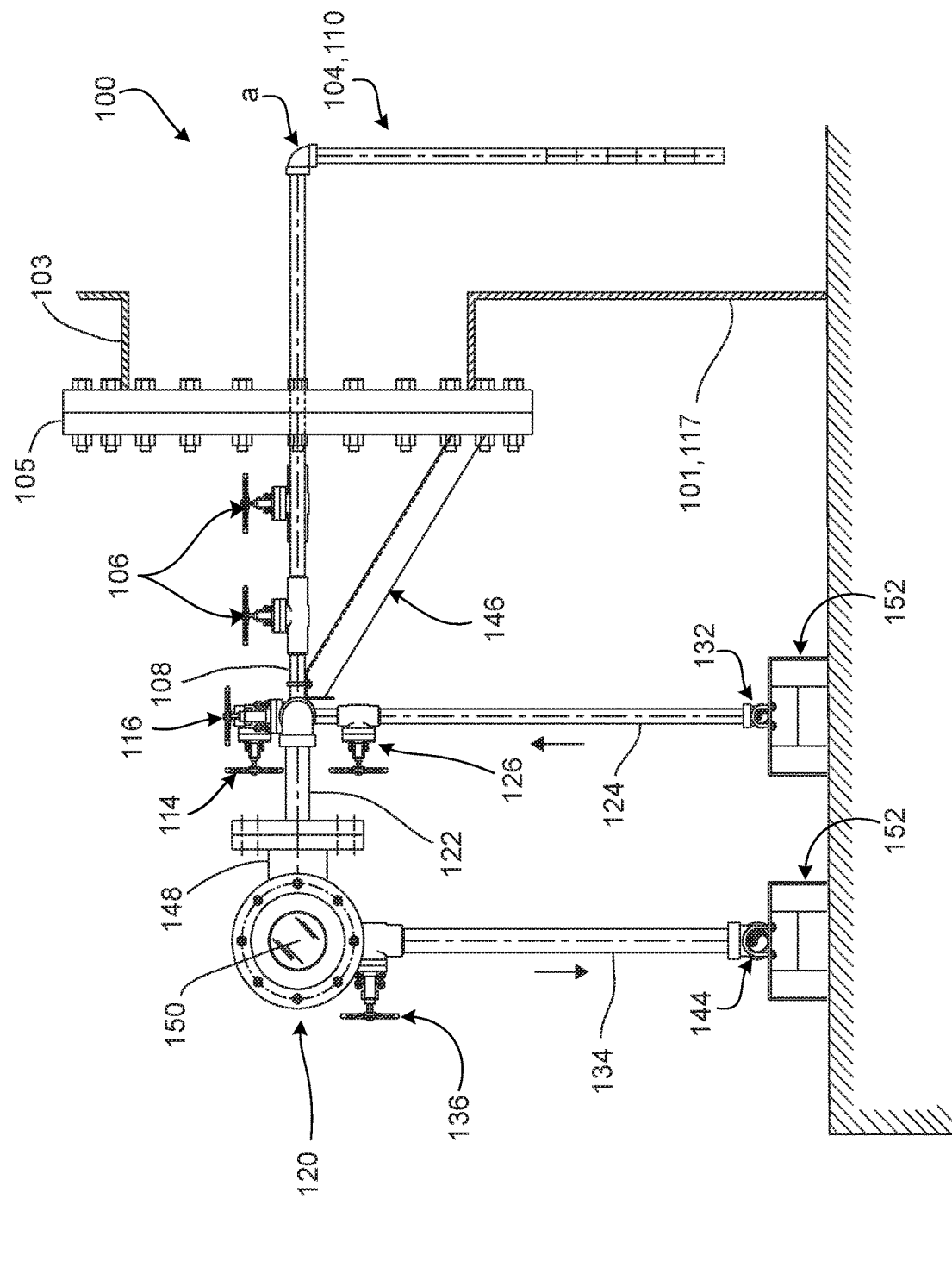
FIG. 4 is a front view of the fluid evaluation device of FIG. 2.

Advantageously, the water cut of the tank 101 may alternatively be determined at the ground level of the tank 101 via any of the manholes 103 (only one manhole 103 shown in FIG. 1) using a different type of device. For example, FIGS. 2-4 illustrate a fluid evaluation device 100 that can be installed to any of the manholes 103 of the tank 101 prior to filling the tank 101 for determining the water cut of the tank 101 subsequent to filling. The fluid evaluation device 100 includes an access cover 105 of a manhole 103, multiple pipes 104 (for example, pipes 104a-104g) that extend through the access cover 105 for sampling fluid within the tank 101, and multiple level valves 106 (for example, level valves 106a-106g) respectively located on exterior portions 108 (for example, exterior portions 108a-108g) of the pipes 104 for selectively closing the pipes 104. The pipes 104 respectively include L-shaped interior portions 110 (for example, L-shaped portions 110a-110g) of differing vertical lengths that extend from the access cover 105 into the tank 101 to respective depths within the tank 101. The level valves 106 are marked (for example, stenciled) with respective vertical lengths of the L-shaped interior portions 110, respective depths of lower ends of the L-shaped interior portions, or respective heights of the lower ends of the L-shaped interior portions above the floor of the tank 101 so that the lengths, depths, or heights can be easily ascertained by an operator.

The fluid evaluation device 100 further includes a common pipe 112 (for example, a header pipe) to which the exterior portions 108 of the pipes 104 extend and several components positioned along the common pipe 112. For example, a vent 114 and a common level valve 116 (for example, a main level valve 116) are positioned along a first segment 118 of the common pipe 112, and an optical device 120 is positioned at an end of a second segment 122 of the common pipe 112 for visualizing fluid flowing from any of the pipes 104 through the common pipe 112. The first and second segments 118, 122 together form an L-shape that positions the optical device 120 at a desired distance from the wall 117 of the tank 101.

The fluid evaluation device 100 further includes a flush pipe 124 extending downward from the common pipe 112, a flush valve 126 positioned along a vertical segment 128 of the flush pipe 124, and an isolation valve 130 positioned along a horizontal segment 132 of the flush pipe 124. The fluid evaluation device 100 is designed for fluid to flow upward through the flush pipe 124. The fluid evaluation device 100 also includes a discharge pipe 134 extending downward from the optical device 120, a discharge valve 136 positioned along a vertical segment 138 of the discharge pipe 134, and a check valve 140 and an isolation valve 142 positioned along a horizontal segment 144 of the discharge pipe 134. The horizontal segments 132, 144 of the flush and discharge pipes 124, 134 are installed to the drain line 111 of the tank, along which a drain valve 119 is positioned. The fluid evaluation device 100 is designed for fluid to flow downward through the discharge pipe 134. The fluid evaluation device 100 also includes an angled support beam 146 that extends from the common pipe 112 to the access cover 105 (refer to FIG. 4).

The optical device 120 includes a t-shaped body 148 that opens to the common pipe 112 at one segment and two viewing windows 150 positioned at opposite, second and third segments. Fluid (for example, crude oil and/or water) flowing through the optical device 120 from the pipes 104 can be easily observed through the viewing windows 150 near the ground level of the tank 101 for determining the water cut of the fluid within the tank 101. The viewing windows 150 typically have a diameter of about 10 cm to about 20 cm and a thickness of about 1 cm to about 3 cm. The viewing windows 150 are typically made of treated glass that can withstand a fluid pressure of up to about 1,380,000 Pa.

In some embodiments, the access cover 105 has a diameter of about 40 cm to about 80 cm. The L-shaped interior portions 110 of the pipes 104 typically have a horizontal length of about 60 cm to about 80 cm and vertical lengths that range from about 50 cm to about 200 cm in equal increments of about 2 cm to about 10 cm. The pipes 104 are typically spaced apart laterally from one another by about 4 cm to about 8 cm and typically have an internal diameter of about 1.5 cm to about 5 cm. The exterior portions 108 of the pipes 104 typically have a length of about 20 cm to about 70 cm, which determines a spacing of the common pipe 112 from the wall 117 of the tank 101. The first segment 118 of the common pipe 112 typically has a length of about 60 cm to about 200 cm. The second segment 122 of the common pipe 112 typically has a length of about 30 cm to about 100 cm, such that the optical device 120 is typically spaced from the wall 117 of the tank 101 by a distance of about 80 cm to about 160 cm.

A height of the common pipe 112 (for example, located at a central height of the manhole 103) above the ground level determines a location of the optical device 120 such that the viewing windows 150 are easily viewable by an operator of the tank 101. Accordingly, the height of the optical device 120 is typically positioned at about 100 cm to about 200 cm above the ground level of the tank 101. The horizontal segment 132 of the flush pipe 124 typically has a length of about 200 cm to about 2000 cm, and the horizontal segment 144 of the discharge pip 132 typically has a length of about 30 cm to about 2000 cm, where both segments 132, 144 feed into the drain line 111 of the tank 101. In some embodiments, the segments 132, 144 may be supported by pipe support bars 152 at the ground level of the tank 101 (refer to FIG. 4). The vertical segment 128 of the flush pipe 124 typically has a length of about 100 cm to about 200 m, and the vertical segment 138 of the discharge pip 132 typically has a length of about 100 cm to about 200 cm.

In some embodiments, the various components of the fluid evaluation device 100 are dimensioned such that the components can be shop fabricated and installed to a manhole 103 without performing hot work on the tank 101, which can reduce an operational down time for installing the fluid evaluation device 100 by up to about 80% and down to about one hour for the case of a 1.15 million barrel tank. The various components of the fluid evaluation device 100 are typically made of carbon steel (for example, the pipes 104 and flanges) or glass (for example, the viewing window 150), and a total cost of producing and installing the fluid evaluation device 100 is typically less than about $5,000.

During a process of filling the tank 101 with crude oil, an amount of water associated with the crude oil is uncertain and variable for many reasons. For example, the amount of water may vary depending on the oil reservoir from which the crude oil was produced or depending on the GOSP at which the crude oil was treated. Therefore, an initial fluid level (for example, an opening fluid height) in the tank 101 is measured, the water cut of the tank 101 is determined using the fluid evaluation device 100, and the volume of water in the tank 101 above the threshold volume (for example, corresponding to fluid height of about 5 cm to about 70 cm above a floor of the tank 101) is subsequently drained from the tank 101 at the drain valve 119 to make the fluid content of the tank 101 acceptable for shipment. Following the draining of the excess water from the tank 101, a final fluid level (for example, a closing fluid height) of the tank 101 is measured to determine the final amount of fluid (for example, crude oil and acceptable volume of water) in the tank 101 for shipment. A final water cut of the tank 101 may also be determined to confirm that the volume of water remaining in the tank 101 is below the threshold volume of water.

Once the tank 101 is filled with fluid via the inlet access 107, the tank 101 is closed off and permitted to settle for about 2 hours (h) to about 4 h while all of the level valves 106 are in a closed state. After the settling period has passed, both isolation valves 130, 142 are opened and maintained in the open state (for example, except during dismantling or maintenance of the fluid evaluation device 100). The drain valve 119 along the drain line 111 of the tank 101 is opened and then closed to maintain a differential pressure between the tank 101 and a discharge receptacle (for example, a slop tank) of at least about 12,410 Pa. Next, the discharge valve 136 and the common level valve 116 are opened to provide a flow path for fluid exiting the pipes 104 through the level valves 106.

The flush valve 126 along the flush pipe 124 (for example, located upstream of the optical device 120) is opened for about 20 seconds (s) to flush the optical device 120 with water flowing from the tank 101, into the drain line 111, and up through the flush pipe 124. A wiper of the optical device is turned in order to clean the viewing windows 150 while the flush valve 126 is open, and then the flush valve 126 is closed. The wiper is typically made of polytetrafluoroethylene and is attached to an interior surface of the viewing window 150. For example, the wiper is hooked with an external arm made of stainless steel that can rotate the wiper about 360 degrees to clean the internal surface of viewing window 150 for maintaining visibility through the viewing window 150.

A selected one of the level valves 106 is opened to permit fluid to flow out of the tank 101 from the respective depth of the L-shaped portion 110 of the pipe 104 on which the selected level valve 106 is disposed, while the other level valves 106 remain closed. In some implementations, an operational requirement provided by shipment requests (for example, related to an allowable water margin) may determine which level valve 106 is selected for initial opening. After about 5 s to about 20 s, the fluid flowing from the selected level valve 106 through the optical device 120 is observed through one or both of the viewing windows 150, and the selected level valve 106 is subsequently closed. A color of the fluid is either determined as black or substantially colorless. If the color of the fluid is black, then the fluid is crude oil, and the L-shaped interior portion 110 of the pipe 104 associated with the selected level valve 106 does not have a vertical length sufficient to access the water that has settled in the bottom region of the tank 101. Therefore, if the fluid is black, then the next level valve 106 with the next longer L-shaped interior portion 110 (for example, that has the next lower depth in the tank 101) is opened, while the other level valves 106 remain closed. Prior to opening the next level valve 106, the optical device 120 is first flushed again by opening the flush valve 126.

Again, the fluid flowing from the open level valve 106 through the optical device 120 is observed through one or both of the viewing windows 150 after about 5 s to about 20 s, and the open level valve 106 is subsequently closed. The process of opening a next level valve 106 positioned on the pipe 104 with the next lower depth in the tank 101 and with the remaining level valves 106 closed and subsequently observing the fluid flowing through the optical device 120 is repeated until the fluid flowing through the optical device 120 is substantially clear. A substantially clear color indicates that the fluid is water, and therefore that the L-shaped interior portion 110 of the pipe 104 associated with the open level valve 106 is accessing the water that has settled in the bottom region of the tank 101. The open level valve 106, the common level valve 116, and the discharge valve 136 are closed to cease the fluid sampling process, and the marked value (for example, the vertical length, depth, or height associated with the L-shaped interior portion 110) on the now closed level valve 106 is notated. This value reflects the water cut of the tank 101. For example, the volume of water in the tank 101 can be calculated from the noted value and a known internal diameter of the tank 101. The tank 101 may be drained accordingly by opening the drain valve 119.

If the color of the fluid observed in the optical device 120 via the first selected level valve 106 is substantially clear, then the L-shaped interior portion 110 of the pipe 104 associated with the first selected level valve 106 has a vertical length that accesses the water that has settled in the bottom region of the tank 101. Therefore, if the fluid is substantially clear, then the next level valve 106 with the next shorter L-shaped interior portion 110 (for example, that has the next higher depth in the tank 101) is opened, while the other level valves 106 remain closed. The process of opening a next level valve 106 positioned on the pipe 104 with the next higher depth in the tank 101 and with the remaining level valves 106 closed and subsequently observing the fluid flowing through the optical device 120 is repeated until the fluid flowing through the optical device 120 is black, indicating that the fluid is crude oil. The open level valve 106, the common level valve 116, and the discharge valve 136 are closed to cease the fluid sampling process, and the marked value on the now closed level valve 106 is notated. This marked value reflects the water cut of the tank 101, and the tank 101 may be drained accordingly by opening the drain valve 119, as discussed above.

Utilizing the fluid evaluation device 100 to determine the water cut of the tank 101 is advantageous to using a conventional dip gauge for several reasons. For example, deploying the fluid evaluation device 100 at the ground level of the tank 101 eliminates the human and operational risks associated with an operator climbing to the roof 115 of the tank 101 to drop the dip gauge into the tank 101. Such risks include falling from the stairway 113 or the top platform 121 (for example, especially during severe weather conditions), excessive physical exertion, personnel exposure to volatile organic compounds (for example, hydrocarbons) and other toxic gases at the top platform 121, human error of a dip gauge reading, and extensive amounts of time associated with climbing the stairway 113 to access the top platform 121. For example, each operator at a tank site is typically required to climb at least two tanks per work shift in order to certify the tanks prior to shipment.

Additionally, the fluid evaluation device 100 can be mechanically installed (for example, bolted) to a manhole 103 in a quick, simple manner that does not require any control systems, cables, or otherwise associated maintenance and calibration procedures. Furthermore, the fluid evaluation device 100 is a closed system in that it prevents direct interaction between fluid in a tank and humans or the environment. That is, an operator can determine a water cut using the optical device 120 without being exposed to toxic gases or liquids. In contrast, conventional methods of determining a water cut using a dip gauge requires an operator to climb to the gauging platform 121, opening a roof hatch, and dip the gauge into the tank 101, during which the operator is directly exposed to toxic gasses and is susceptible to high altitude risks. The fluid evaluation device 100 can be installed to any floating roof tank 101 and does not require any significant modifications to the wall 117 of the tank 101, as the fluid evaluation device 100 utilizes an existing structure (for example, a flange) of a manhole 103 without obstructing hatches of the manhole 103. The fluid evaluation device 100 is also capable of taking advantage of the existing head pressure of the fluid within the tank 101 to ensure fluid flow to the discharge receptacle at a lower head pressure for viewing the fluid at a height of the optical device 120.

Furthermore, an accuracy of the fluid evaluation device 100 has been determined to be comparable to (for example, as good as) that of a conventional dip gauge. For example, Table 1 provides initial tank fluid levels, water cuts before draining using both the fluid evaluation device 100 and a conventional dip gauge, final tank fluid levels, and water cuts after draining using the fluid evaluation device 100 for multiple tanks on multiple occasions. As apparent from Table 1, the fluid evaluation device 100 can perform adequately without the risks associated with employing a dip gauge.

TABLE 1

Water cut evaluation of various tanks determined using a conventional dip gauge and the fluid evaluation device 100.

| Tank | Initial Tank Fluid Level (m) | Water Cut Before Draining (Dip Gauge) (cm) | Water Cut Before Draining (Fluid Evaluation Device 100) (cm) | Final Tank Fluid Level (m) | Water Cut After Draining (Fluid Evaluation Device 100) (cm) |
|---|---|---|---|---|---|
| Tank #1 | 16.75 | 25.4 | 25.4 | 16.64 | 15.24 |
| Tank #2 | 11.33 | 36.58 | 36.58 | 11.26 | 27.94 |
| Tank #3 | 17.64 | 30.48 | 30.48 | 17.53 | 20.32 |
| Tank #4 | 17.61 | 25.4 | 25.4 | 17.56 | 20.32 |
| Tank #5 | 17.64 | 7.62 | Below 17.78 | 17.64 | 7.62 |
| Tank #6 | 17.65 | Open Drain | Below 17.78 | 17.57 | No Water |

Regular preventive maintenance activities can be performed to the fluid evaluation device 100 to ensure mechanical and functional integrity. For example, with all valves located between the access cover 105 and the drain line 111 in a closed state, stems of the valve may be cleaned and greased. Additionally, base flanges of the viewing windows 150 that include wiper assemblies may be dismantled and cleaned along internal surfaces. In some examples, line maintenance activities may be performed when there is blockage of a pipe 104 of the fluid evaluation device 100. For example, the common level valve 116 and the flush valve 126 are closed, a water source of about 206,842 Pa is connected to the vent 114, and the level valve 106 of the clogged pipe 104 is opened to flush the clogged pipe 104 with water flowing from the vent 114 into the tank 101. To return the fluid evaluation device 100 to an operational state, the vent 114 is plugged, and the pipe 104 is closed again.

Figure 5:
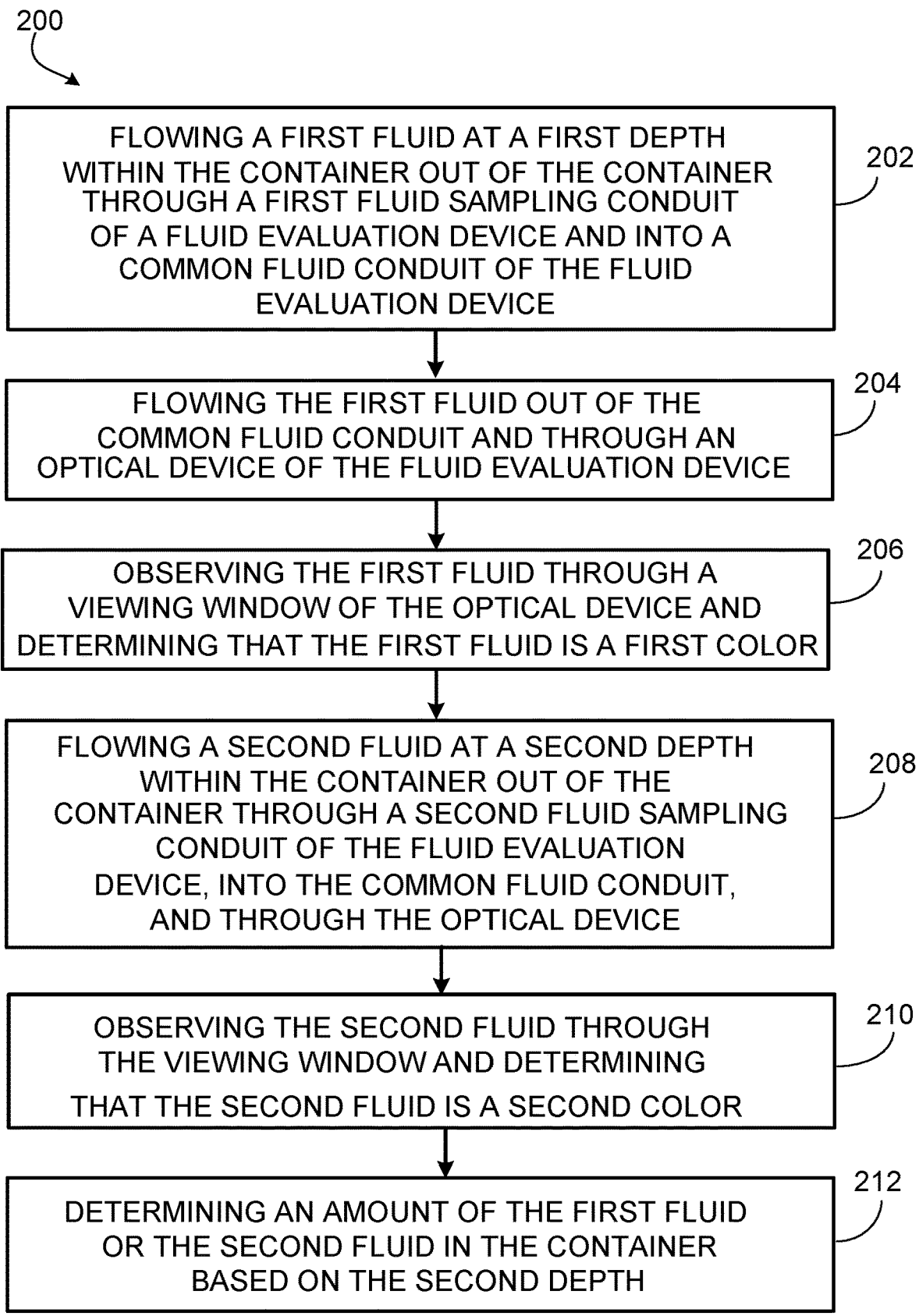
FIG. 5 is a flow chart illustrating an example method of analyzing a fluid content within a container.

FIG. 5 is a flow chart illustrating an example method 200 of analyzing a fluid content within a container (for example, the tank 101). In some embodiments, the method 200 includes flowing a first fluid at a first depth within the container out of the container through a first fluid sampling conduit (for example, a pipe 104) of a fluid evaluation device (for example, the fluid evaluation device 100) and into a common fluid conduit (for example, the common pipe 112) of the fluid evaluation device (202). In some embodiments, the method 200 further includes flowing the first fluid out of the common fluid conduit and through an optical device (for example, the optical device 120) of the fluid evaluation device (204). In some embodiments, the method 200 further includes observing the first fluid through a viewing window (for example, the viewing window 150) of the optical device and determining that the first fluid is a first color (206). In some embodiments, the method 200 further includes flowing a second fluid at a second depth within the container out of the container through a second fluid sampling conduit (for example, a pipe 104) of the fluid evaluation device, into the common fluid conduit, and through the optical device (208). In some embodiments, the method 200 further includes observing the second fluid through the viewing window and determining that the second fluid is a second color (210). In some embodiments, the method 200 further includes determining an amount of the first fluid or the second fluid in the container based on the second depth (212).

While the fluid evaluation device 100 has been described and illustrated with respect to certain dimensions, sizes, shapes, arrangements, materials, methods 200, and tanks 101, in some embodiments, a fluid evaluation device that is otherwise substantially similar in construction and function to the fluid evaluation device 100 may include one or more different dimensions, sizes, shapes, arrangements, and materials or may be utilized according to different methods or with different tanks. For example, while the fluid evaluation device 100 is illustrated as including seven L-shaped sampling pipes 104, in some embodiments, a fluid evaluation device that is otherwise substantially similar in construction and function to the fluid evaluation device 100 may include a different number of L-shaped sampling pipes.

While the fluid evaluation device 100 has been described and illustrated as being utilized to analyze crude oil produced at GOSPs, in some embodiments, the fluid evaluation device 100 may also be utilized to analyze refined hydrocarbon liquid-form gases produced at refineries.

Other embodiments are also within the scope of the following claims.

What is claimed is:

1. A fluid evaluation device for analyzing a fluid content within a container, the fluid evaluation device comprising:
   first and second fluid sampling conduits passing laterally into the container at a same height and respectively extending to first and second vertical depths below the height within fluid stored in the container;
   a common fluid conduit oriented horizontally and to which the first and second fluid sampling conduits extend for receiving fluid flowing out of the container through either of the first or second sampling conduits; and
   an optical device positioned along the common fluid conduit and comprising a viewing window for observing fluid flowing therethrough from the common fluid conduit.

2. The fluid evaluation device of claim 1, wherein the first and second fluid sampling conduits have an L-shape.

3. The fluid evaluation device of claim 1, further comprising a plate through which the first and second fluid sampling conduits pass laterally into the container.

4. The fluid evaluation device of claim 3, wherein the plate is configured to cover an access opening of the container.

5. The fluid evaluation device of claim 1, further comprising first and second valves respectively arranged along the first and second fluid sampling conduits for selectively opening and closing the first and second fluid sampling conduits to fluid flow.

6. The fluid evaluation device of claim 1, further comprising first and second markings respectively indicating or corresponding to the first and second vertical depths of the first and second fluid sampling conduits.

7. The fluid evaluation device of claim 1, wherein the first and second fluid sampling conduits have vertical lengths in a range of about 50 cm to about 200 cm.

8. The fluid evaluation device of claim 1, wherein a difference in a vertical length between the first and second fluid sampling conduits is about 2 cm to about 10 cm.

9. The fluid evaluation device of claim 1, wherein the first and second vertical depths are located in a range of about 2.5 cm to about 150 cm above a floor of the container.

10. The fluid evaluation device of claim 1, wherein the first and second fluid sampling conduits are spaced laterally from each other by about 4 cm to about 8 cm.

11. The fluid evaluation device of claim 1, further comprising a discharge fluid conduit coupled to the common fluid conduit for receiving the fluid flowing from the common fluid conduit and directing the fluid away from the container.

12. The fluid evaluation device of claim 11, wherein the optical device is arranged between the common fluid conduit and the discharge fluid conduit such that the optical device is located downstream of the common fluid conduit and upstream of the discharge fluid conduit.

13. The fluid evaluation device of claim 1, wherein the viewing window is a first viewing window, and wherein the optical device further comprises a second viewing window disposed opposite the first viewing window.

14. The fluid evaluation device of claim 13, wherein the optical device further comprises a body having a t-shape, and wherein the first and second viewing windows are disposed at opposite ends of the body.

15. The fluid evaluation device of claim 1, wherein the viewing window comprises a glass viewing window.

16. The fluid evaluation device of claim 1, wherein the optical device is positioned at a height of about 100 cm to about 200 cm above a ground level at which the container is positioned.

17. The fluid evaluation device of claim 1, further comprising one or more additional fluid sampling conduits passing laterally into the container at the same height, respectively extending to one or more vertical depths below the height within the fluid stored in the container, and extending to the common fluid conduit.

18. The fluid evaluation device of claim 1, wherein the container contains crude oil and water.

19. The fluid evaluation device of claim 1, wherein the fluid content of the container comprises a water cut of a crude oil tank.

20. The fluid evaluation device of claim 1, wherein the optical device is vertically positioned at the same height.

21. A method of analyzing a fluid content within a container, the method comprising:

flowing a first fluid at a first vertical depth within the container out of the container through a first fluid sampling conduit of a fluid evaluation device passing laterally into the container at a height above the first vertical depth and into a common fluid conduit of the fluid evaluation device, the common fluid conduit being oriented horizontally;

flowing the first fluid out of the common fluid conduit and through an optical device of the fluid evaluation device;

observing the first fluid through a viewing window of the optical device and determining that the first fluid is a first color;

flowing a second fluid at a second vertical depth within the container out of the container through a second fluid sampling conduit of the fluid evaluation device passing laterally into the container at the same height, into the common fluid conduit, and through the optical device, the height being above the second vertical depth;

observing the second fluid through the viewing window and determining that the second fluid is a second color; and determining an amount of the first fluid or the second fluid in the container based on the second depth.

22. The method of claim 21, wherein the optical device is located at about 100 cm to about 200 cm above a ground level at which the container is positioned.

23. The method of claim 21, further comprising stopping a flow of the first fluid out of the container after determining that the first fluid is the first color and before flowing the second fluid out of the container.

24. The method of claim 21, further comprising reading an indication of the second vertical depth from a marking on the fluid evaluation device.

25. The method of claim 21, wherein the first color is black, the first fluid comprises crude oil, and the second fluid comprises water.

26. The method of claim 25, wherein the second vertical depth is lower than the first vertical depth.

27. The method of claim 21, wherein the second color is black, the first fluid comprises water, and the second fluid comprises crude oil.

28. The method of claim 27, wherein the first vertical depth is lower than the second vertical depth.

29. The method of claim 21, wherein the viewing window is a first viewing window, and wherein the optical device further comprises a second viewing window disposed opposite the first viewing window.

30. The method of claim 29, wherein the optical device further comprises a body having a t-shape, and wherein the first and second viewing windows are disposed at opposite ends of the body.

31. The method of claim 21, wherein determining an amount of the first fluid or the second fluid in the container comprises determining a water cut of a crude oil tank.

* * * * *